United States Patent
Bedor

(10) Patent No.: US 8,236,035 B1
(45) Date of Patent: Aug. 7, 2012

(54) SPINAL FIXATION SYSTEM AND METHOD

(76) Inventor: Bernard M. Bedor, Ponte Vedra Beach, FL (US)

( * ) Notice: Subject to any disclaimer, the term of this patent is extended or adjusted under 35 U.S.C. 154(b) by 249 days.

(21) Appl. No.: 12/485,426

(22) Filed: Jun. 16, 2009

(51) Int. Cl.
*A61B 17/84* (2006.01)

(52) U.S. Cl. .......... 606/328; 606/266; 606/272

(58) Field of Classification Search .......... 606/246–279, 606/300–303, 305–309, 319, 320, 322, 328; 411/437
See application file for complete search history.

(56) References Cited

U.S. PATENT DOCUMENTS

| | | | |
|---|---|---|---|
| 4,781,507 A * | 11/1988 | Duenas | 411/433 |
| 5,030,220 A | 7/1991 | Howland | |
| 5,207,678 A | 5/1993 | Harms et al. | |
| 5,466,237 A | 11/1995 | Byrd, III et al. | |
| 5,474,555 A | 12/1995 | Puno et al. | |
| 5,487,744 A | 1/1996 | Howland | |
| 5,496,321 A | 3/1996 | Puno et al. | |
| 5,624,442 A | 4/1997 | Mellinger et al. | |
| 5,649,926 A | 7/1997 | Howland | |
| 5,776,134 A | 7/1998 | Howland | |
| 5,782,833 A | 7/1998 | Haider | |
| 6,540,748 B2 | 4/2003 | Lombardo | |
| 6,565,565 B1 | 5/2003 | Yuan et al. | |
| 6,565,567 B1 | 5/2003 | Haider | |
| 6,585,737 B1 | 7/2003 | Baccelli et al. | |
| 6,896,677 B1 * | 5/2005 | Lin | 606/266 |
| 6,974,291 B2 * | 12/2005 | Li | 411/437 |
| 7,077,864 B2 | 7/2006 | Byrd, III et al. | |
| 7,125,426 B2 | 10/2006 | Moumene et al. | |
| 7,141,051 B2 | 11/2006 | Janowski et al. | |
| 2003/0125741 A1 * | 7/2003 | Biedermann et al. | 606/61 |
| 2005/0055026 A1 | 3/2005 | Biedermann et al. | |
| 2005/0131410 A1 * | 6/2005 | Lin | 606/61 |
| 2005/0261687 A1 | 11/2005 | Garamszegi et al. | |
| 2006/0064089 A1 | 3/2006 | Jackson | |
| 2006/0084981 A1 | 4/2006 | Shluzas | |
| 2006/0149241 A1 * | 7/2006 | Richelsoph et al. | 606/61 |
| 2006/0161152 A1 | 7/2006 | Ensign et al. | |
| 2006/0161153 A1 | 7/2006 | Hawkes et al. | |

(Continued)

FOREIGN PATENT DOCUMENTS

EP 1800613 A1 6/2007

(Continued)

OTHER PUBLICATIONS www.dictionary.reference.com/browse/slot. p. 3, accessed on Sep. 1, 2011.*

*Primary Examiner* — Eduardo C Robert
*Assistant Examiner* — Atiya Mahmud
(74) *Attorney, Agent, or Firm* — Jason S. Miller; Lowndes, Drosdick, Doster, Kantor & Reed, P.A.

(57) ABSTRACT

A spinal fixation system (1) for use in the fixation of a spine comprising: a coupling element (2) having a pair of opposed longitudinal apertures (17) through a wall (35) thereof; a longitudinal slot (8) in a coupling element (2) interior surface (3); a hole (13) through the bottom end (5) of the coupling element (2); and a securing element (18) dimensioned for insertion into the coupling element (2), the securing element (18) having an outwardly extending wing (26) dimensioned for riding in the coupling element slot (8), for preventing a rotation of the securing element (18) about a longitudinal axis (7) thereof.

10 Claims, 5 Drawing Sheets

U.S. PATENT DOCUMENTS

| | | |
|---|---|---|
| 2006/0200128 A1 | 9/2006 | Mueller |
| 2006/0235393 A1* | 10/2006 | Bono et al. ............... 606/61 |
| 2006/0247636 A1 | 11/2006 | Yuan et al. |
| 2007/0043358 A1* | 2/2007 | Molz et al. ............... 606/61 |
| 2007/0093826 A1 | 4/2007 | Hawkes et al. |
| 2007/0270813 A1 | 11/2007 | Garamszegi |
| 2007/0282337 A1 | 12/2007 | Garamszegi |
| 2008/0045953 A1 | 2/2008 | Garamszegi |
| 2008/0045955 A1 | 2/2008 | Berrevoets et al. |
| 2008/0183215 A1* | 7/2008 | Altarac et al. ............ 606/265 |
| 2008/0262548 A1 | 10/2008 | Lange et al. |
| 2008/0269809 A1 | 10/2008 | Garamszegi |
| 2009/0030457 A1 | 1/2009 | Janowski et al. |
| 2009/0076550 A1 | 3/2009 | Bernhardt, Jr. et al. |
| 2009/0082819 A1 | 3/2009 | Blain et al. |
| 2009/0105716 A1 | 4/2009 | Barrus |
| 2009/0105769 A1 | 4/2009 | Rock et al. |
| 2009/0105770 A1* | 4/2009 | Berrevoets et al. ......... 606/308 |

FOREIGN PATENT DOCUMENTS

| | | |
|---|---|---|
| WO | 2006130179 A2 | 12/2006 |
| WO | 2009015100 A2 | 1/2009 |
| WO | 2009055400 A1 | 4/2009 |

* cited by examiner

SPINAL FIXATION SYSTEM AND METHOD

BACKGROUND OF THE INVENTION

1. Field of the Invention

The present invention relates to spinal fixation systems and methods, more specifically, a spinal fixation system that provides retention of a fixation rod wherein lateral and rotational movement of a fixation rod and bone fixation element are significantly reduced.

2. Description of Related Art

Spinal fixation, also referred to as vertebral fixation, is a neurosurgical procedure for reducing movement of a spine so as to decrease damage to the spinal cord and/or spinal roots. Spinal fixation is utilized to treat a wide variety of spinal disorders and deformities which result in vertebral displacement of the spine, including, but not limited to, scoliosis, kyphosis, spondylolisthesis, rotation, tumor diseases, disc degeneration, and congenital defects. In addition, spinal fixation is utilized to treat vertebral fractures, injuries, or other traumas to the spine wherein the spine becomes displaced from such fracture, injury, or trauma.

The procedure utilizes synthetic devices to anchor two or more vertebrae to one another in the spinal column. Such devices may include bone fixation elements, also referred to as bone screws, coupled to a spinal fixation rod via a coupling element. The bone fixation elements are inserted into the pedicle(s) of the desired vertebrae and are secured to or within the coupling element. The spinal fixation rod, in turn, is secured within the coupling element via a securing element. Accordingly, the spinal fixation rod is ultimately secured to the vertebrae such that movement of the stabilized vertebrae is limited. As the ultimate goal of spinal fixation is to limit movement of the spine, it is of great importance that fixation between the bone fixation element, coupling element, and fixation rod be rigid and permanent.

Various structures for securing the fixation rod within the coupling element are currently available. One such structure includes the use of a compression means, such as a compression screw, which exerts a predetermined amount of force on the fixation rod when the compression means is secured within the coupling element. Such compressive force also translates to a compressive force being applied on the coupling element and the bone fixation element as well, thereby reducing movement of the synthetic devices within the vertebra to which such synthetic devices are secured.

However, some synthetic devices require the bone fixation element to be secured within the coupling element at a substantially 90 degree angle thereto, thereby resulting in a substantially 90 degree insertion of the bone fixation element into the pedicle. Thus, use of such synthetic devices limits the ability to secure such devices at an angle customized to a patient, even if a more accurate and secure fixation would result if the bone fixation element were inserted into the pedicle at either an acute or obtuse angle. As such, there exists a need for an improved spinal fixation system that would permit rotational movement of a bone fixation element within the coupling element prior to insertion into a pedicle, but prevent movement thereof after insertion into the pedicle.

Moreover, although the compression means utilized in some synthetic devices results in a reduction of movement of the fixation rod within the coupling element, rotational movement of the fixation rod therein does not always result, as in some cases the compression means is not shaped so as to maximize the surface area contact between the compression means and the fixation rod. As such, there exists a need for an improved spinal fixation system that would limit both lateral and rotational movement of a fixation rod located within a coupling element.

Furthermore, some synthetic devices utilizing compression means may become loose over time due to vibrational forces applied thereto, thereby resulting in pain and discomfort in the patient and a need to perform corrective surgical procedures to re-tighten and re-secure the synthetic devices. As such, there exists a need for an improved spinal fixation system which would limit loosening of the synthetic devices due to vibrational forces.

SUMMARY OF THE INVENTION

The present invention is directed to a spinal fixation system having a coupling element having: a pair of opposed longitudinal apertures through a wall thereof extending from a top end of the coupling element to an aperture bottom in spaced relation from a bottom end of the coupling element, the wall defining an interior space dimensioned for admitting a bone fixation element thereinto, the apertures dimensioned for admitting a fixation rod diametrically through the interior space; a longitudinal slot in an interior surface of the coupling element extending from the coupling element top end to a slot bottom in spaced relation from the coupling element bottom end; a hole through the bottom end dimensioned for admitting a shank of the elongated bone fixation element therethrough and smaller than a head of the bone fixation element for retaining the head within the interior space, the shank extending downwardly from the fixation element; and a securing element dimensioned for vertical slidable insertion into the coupling element interior space atop the fixation element head, the securing element having an outwardly extending wing dimensioned for riding in the coupling element slot, for preventing a rotation of the securing element about a longitudinal axis thereof.

The present invention is also directed to a method for fixating a spine comprising positioning a coupling element having: a pair of opposed longitudinal apertures through a wall thereof extending from a top end of the coupling element to an aperture bottom in spaced relation from a bottom end of the coupling element, the wall defining an interior space dimensioned for admitting a bone fixation element thereinto, the apertures dimensioned for admitting a fixation rod diametrically through the interior space; a longitudinal slot in an interior surface of the coupling element extending from the coupling element top end to a slot bottom in spaced relation from the coupling element bottom end; and a hole through the bottom end dimensioned for admitting a shank of the elongated bone fixation element therethrough and smaller than a head of the bone fixation element for retaining the head within the interior space, the shank extending downwardly from the bone fixation element to a bone in a spine; inserting a bone fixation element into the coupling element such that a shank of the bone fixation element is located within the interior space and the tip extends into the hole and is adjacent to the bone; driving the bone fixation element into the bone such that at least a portion of a shank of the bone fixation element extends through the hole and into the bone; admitting a fixation rod into a pair of opposed longitudinal apertures though a wall of the coupling element; inserting an outwardly extending wing of a securing element into the coupling element slot, wherein the outwardly extending wing is dimensioned for riding in the coupling element slot; and securing the securing element within the coupling element to prevent rotation of the securing element about a longitudinal axis thereof.

DETAILED DESCRIPTION OF THE PREFERRED EMBODIMENTS

A description of the preferred embodiments of the present invention will now be presented.

Figure 1:
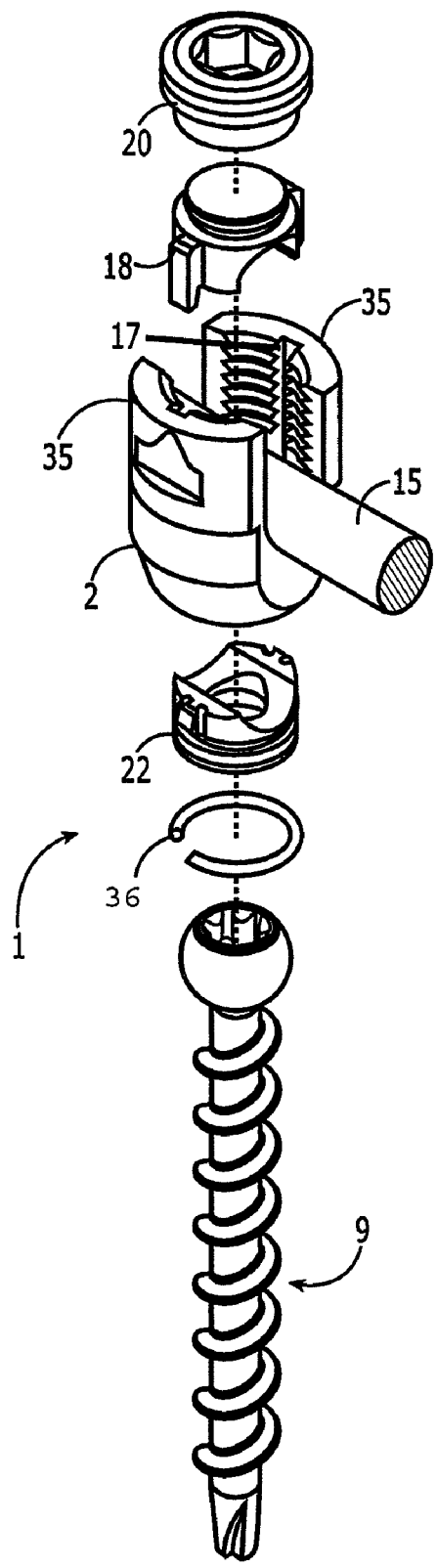
FIG. 1 is an isometric exploded view of spinal fixation system of the present invention.

With reference to FIG. 1, an isometric exploded view of spinal fixation system of the present invention is shown. The spinal fixation system 1 of the present invention includes a coupling element 2 having walls 35 and at least one longitudinal aperture 17 and a securing element 18. When used in spinal fixation, a bone fixation element 9 and a fixation rod 15 are utilized. The spinal fixation system 1 of the present invention may also include one optional locking element 20, a washer 36, and a retaining element 22.

Figure 2:
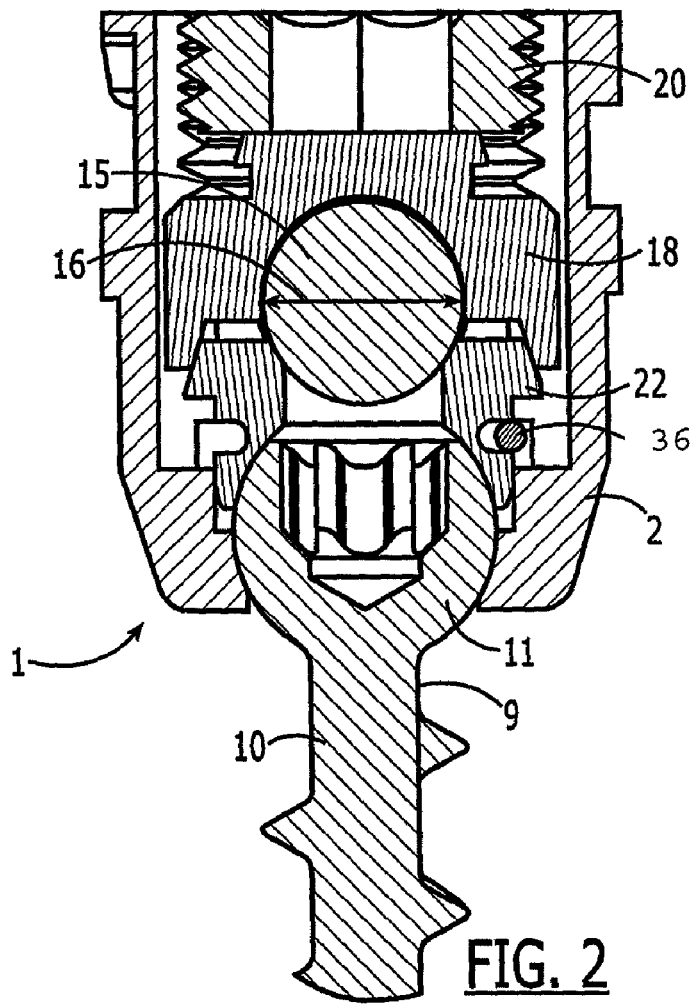
FIG. 2 is a cross-sectional view of an assembled spinal fixation system of the present invention.
Figure 3:
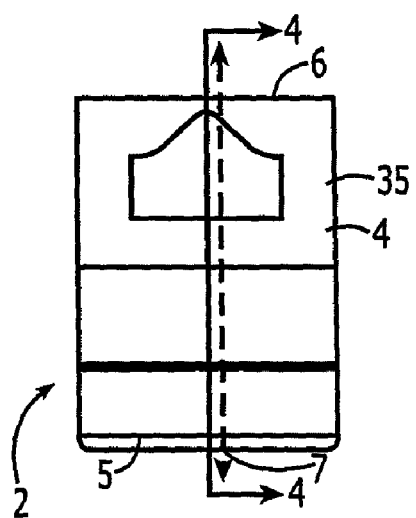
FIG. 3 is a side view of a coupling element of the spinal fixation system of the present invention.
Figure 4:
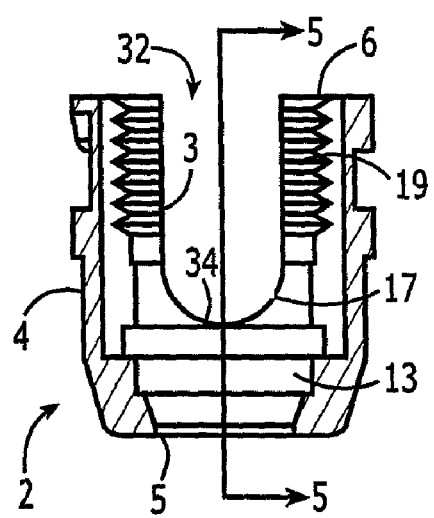
FIG. 4 is a cross-sectional view along lines 4-4 of the embodiment of FIG. 3.
Figure 5:
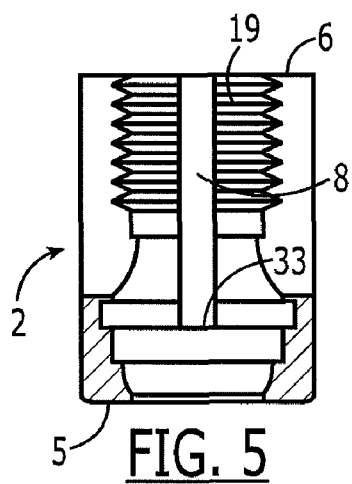
FIG. 5 is a cross-sectional view along lines 5-5 of the embodiment of FIG. 4.
Figure 6:
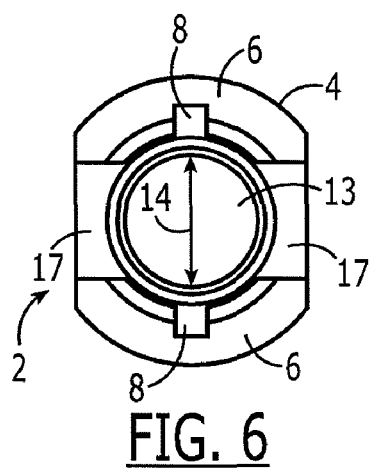
FIG. 6 is a top view of a coupling element of the spinal fixation system of the present invention.
Figure 7:
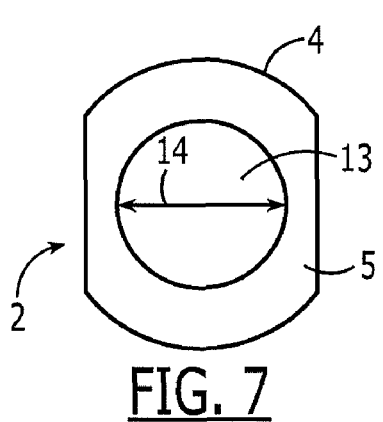
FIG. 7 is a bottom view of a coupling element of the spinal fixation system of the present invention.

In FIG. 2, a cross-sectional view of an assembled spinal fixation system of the present invention having all of the elements shown in FIG. 1 is shown. When assembled, the spinal fixation system 1 permits rigid fixation of the fixation rod 15 wherein a constant force is applied on the fixation rod 15 and rigid fixation of the bone fixation element 9 wherein a constant force is applied on the fixation element 9.

When assembled, the bone fixation element 9 is secured within the coupling element 2 such that a head 11 of the bone fixation element 9 is retained within the coupling element 2 while a shank 10 of the bone fixation element 9 extends through the coupling element 2. An optional washer 36 may be inserted into the coupling element 2 such that the washer 36 is located above and adjacent to the head 11 of the bone fixation element 9. An optional retaining element 22 may be inserted into the coupling element 2 wherein the retaining element 22 is located atop the washer 36 and bone fixation element 9.

The fixation rod 15, which has a diameter 16, is admitted through the apertures 17 of the coupling element 2. The retaining element 22, if utilized, is located between fixation rod 15 and the head 11 of the bone fixation element 9. The securing element 18 is secured within the coupling element 2. If a locking element 20 is utilized, the securing element 18 is secured thereto and both are ultimately secured within the coupling element 2.

When the spinal fixation system 1 is assembled, a substantially constant force is applied to the fixation rod 15, retaining element 22, and bone fixation element 9. However, if no retaining element 22 is utilized, then the substantially constant force is only applied to the fixation rod 15 and the bone fixation element 9.

FIGS. 3-7 show varying views of a coupling element of the spinal fixation system of the present invention. The coupling element 2 has an exterior surface 4, a bottom end 5, a top end 6, and a longitudinal axis 7. The coupling element 2 also has a pair of opposed longitudinal apertures 17 through a wall 35 thereof extending from a top end 6 of the coupling element 2 to an aperture bottom 34 in spaced relation from a bottom end 5 of the coupling element 2. The apertures 17 may be substantially U-shaped as shown, but other shapes may also be utilized.

The wall 35 defines an interior space 32 dimensioned for admitting a bone fixation element 9 thereinto and the apertures 17 are dimensioned for admitting a fixation rod 15 diametrically through the interior space 32 of the coupling element 2. The coupling element 2 also includes a slot 8 in an interior surface 3 of the coupling element 2 extending from the coupling element 2 top end 6 to a slot bottom 33 in spaced relation from the coupling element 2 bottom end 5. As shown, the apertures 17 are angularly offset with respect to the slots 8. The coupling element 2 also includes a hole 13 through the bottom end 5 of the coupling element 2.

An optional mating element 19 may be located on an interior surface 3 of the coupling element 2. As shown, the mating element 19 may be threads; however, other mating elements may also be utilized.

The hole 13 has a diameter 14 and is dimensioned for admitting a shank 10 of the elongated bone fixation element 9 therethrough (shown in FIG. 2) and smaller than a head 11 of the bone fixation element 9 (shown in FIG. 2) for retaining the head 11 within the interior space 32 of the coupling element 2. As shown, the hole 13 is dimensioned for housing a substantially round bone fixation element head 11 (shown in FIGS. 1, 2, and 13), thereby permitting rotational movement of the bone fixation element 9. However, the hole 13 may be of other dimensions as well, including, but not limited to, planar or convex.

Figure 8:
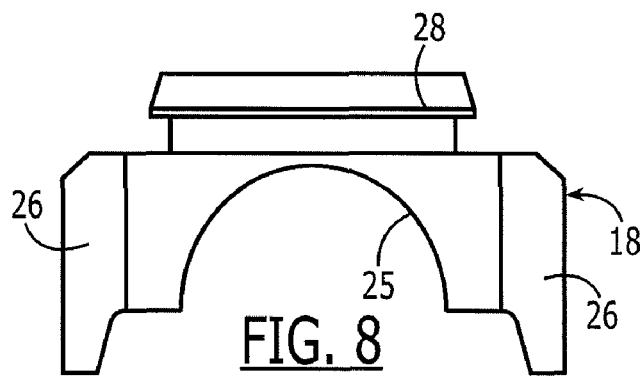
FIG. 8 is a side view of a securing element of the spinal fixation system of the present invention.
Figure 9:
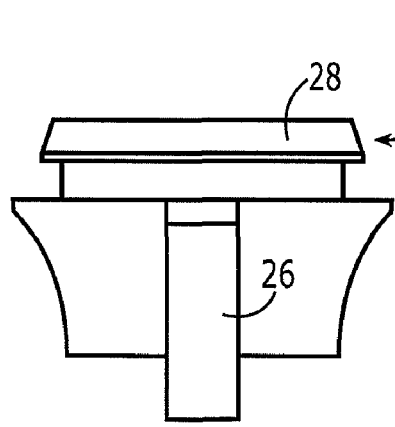
FIG. 9 is an alternate side view of a securing element of the spinal fixation system of the present invention.
Figure 10:
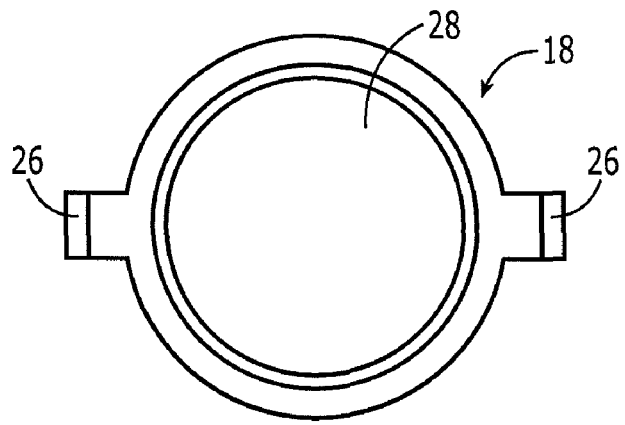
FIG. 10 is a top view of a securing element of the spinal fixation system of the present invention.

FIGS. 8, 9, and 10 show varying views of a securing element of the spinal fixation system of the present invention. The securing element 18 has at least one outwardly extending wing 27 dimensioned for riding in the slot 8 of the coupling element 2 for preventing a rotation of the securing element 18 about a longitudinal axis 7. The securing element 18 may include an upwardly extending arm 28 dimensioned for insertion into the locking element 20. As shown, the arm 28 is substantially T-shaped; however, other shapes may be utilized. The securing element bottom surface 25 may be substantially concave for at least partially circumscribing the diameter 16 of the bone fixation rod 15.

Figure 11:
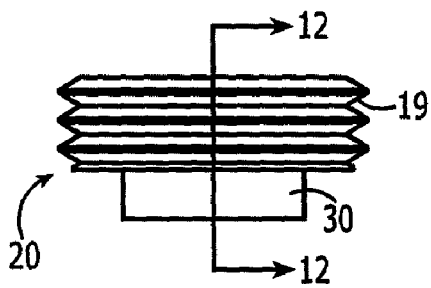
FIG. 11 is a side view of a locking element of the spinal fixation system of the present invention.
Figure 12:
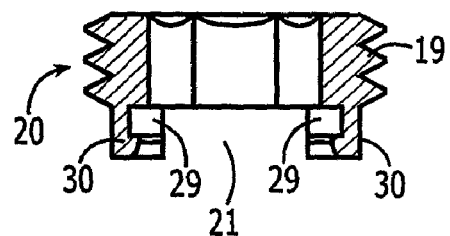
FIG. 12 is a cross-sectional view along lines 12-12 of the embodiment of FIG. 11.

FIGS. 11 and 12 show varying views of a locking element of the spinal fixation system of the present invention. The locking element 20, which is an optional component of the spinal fixation system 1 of the present invention, may include a mating element 19 located on an external surface thereon and a downwardly extending wall 30. The wall 30 defines a locking element interior space 21 dimensioned for housing the arm 28 of the securing element 18 and may include at least one groove 29 located therein. Moreover, the wall 30 may be sized and shaped so as to prevent the arm 28 from dislodging, yet permit rotation of the arm 28 therein. In this manner, the securing element 18 is rotatingly secured to the locking element 20.

Figure 13:
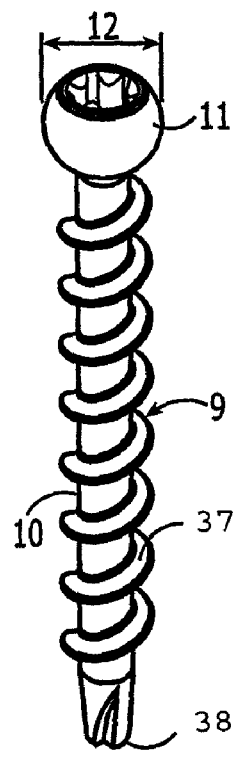
FIG. 13 is a perspective view of a bone fixation element of the spinal fixation system of the present invention.

Next, FIG. 13 shows a perspective view of a bone fixation element of the spinal fixation system of the present invention. The bone fixation element 9 may be a bone screw or any other type of fastener that may be utilized for insertion into a bone. The bone fixation element 9 includes a head 11, an elongated shank 10 which extends downwardly from the bone fixation element 9, and a tip 38. Bone fixation element threads 37 may be located on the shank 10 of the bone fixation element 9.

The head 11 of the bone fixation element 9 is of a certain size and shape and may have a certain diameter 12. The diameter 12 may be of any size; however, the diameter 12 should be greater than the hole diameter 14 in the coupling element 2 so as to allow the head 11 of the bone fixation element 9 to remain within the coupling element 2 while the shank 10 of the bone fixation element 9 extends through the hole 13 of the coupling element 2. The head 11 of the bone fixation element 9 may be round in shape to permit rotational movement of the bone fixation element 9 within the coupling means 2 when the hole 13 is dimensioned as such, for example, when the hole 13 is substantially concave. In this manner, when the bone fixation element 9 is inserted through the hole 13 of the coupling element 2, it still may be rotated and adjusted to a desired angle prior to insertion into a bone. Although the head 11 of the bone fixation element 9 is shown having a substantially round shape, other shapes may be utilized.

Figure 14:
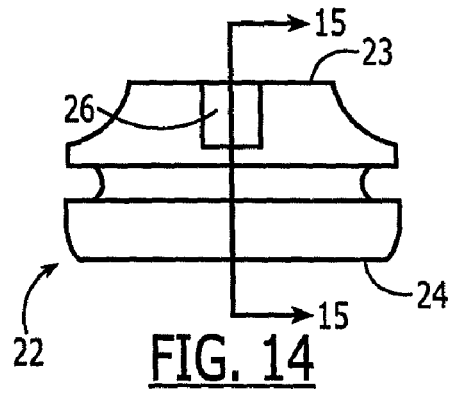
FIG. 14 is a side view of a retaining element of the spinal fixation system of the present invention.
Figure 15:
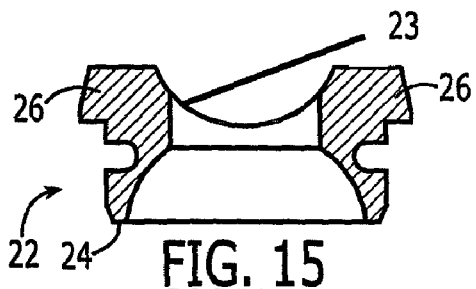
FIG. 15 is a cross-sectional view along lines 15-15 of the embodiment of FIG. 14.
Figure 16:
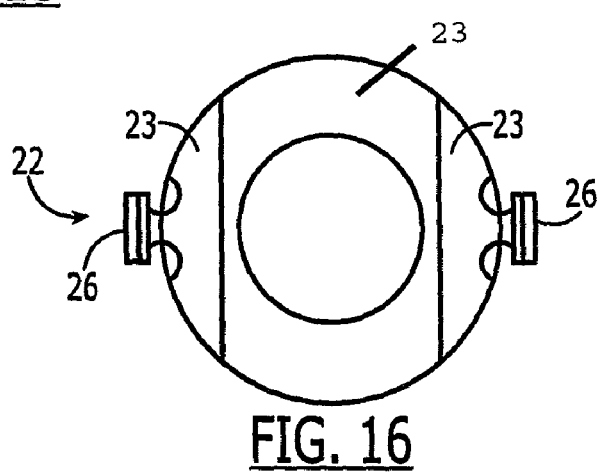
FIG. 16 is a top view of a retaining element of the spinal fixation system of the present invention.

With respect to FIGS. 14, 15, and 16, varying views of a retaining element of the spinal fixation system of the present invention are shown. The retaining element 22 is an optional element of the spinal fixation system 1 of the present invention and includes a top surface 23 and a bottom surface 24. The retaining element 22 may also include at least one outwardly extending wing 26 dimensioned for riding in the slot 8 of the coupling element 2 and for preventing a rotation of the retaining element 22 about a longitudinal axis 7. The top surface 23 of the retaining element 22 may be substantially concave for at least partially circumscribing the diameter 16 of the bone fixation rod 15 when the fixation rod 15 is admitted into the apertures 17 of the coupling element 2, thereby resulting in a greater surface area contact between the fixation rod 15 and the top surface 23 of the retaining element 22. Although a substantially concave top surface 23 is shown, the top surface 23 may also be of any other form including, but not limited to, planar or convex.

The bottom surface 24 of the retaining element 22 may be generally spherically-shaped so as to accommodate at least a portion of the head 11 of the bone fixation element 9. In this manner, limited motion between the bone fixation element 9 and the retaining element 22 is permitted. Although the bottom surface 24 of the retaining element 22 is shown having a generally spherical shape, other shapes may also be utilized.

Figure 17:
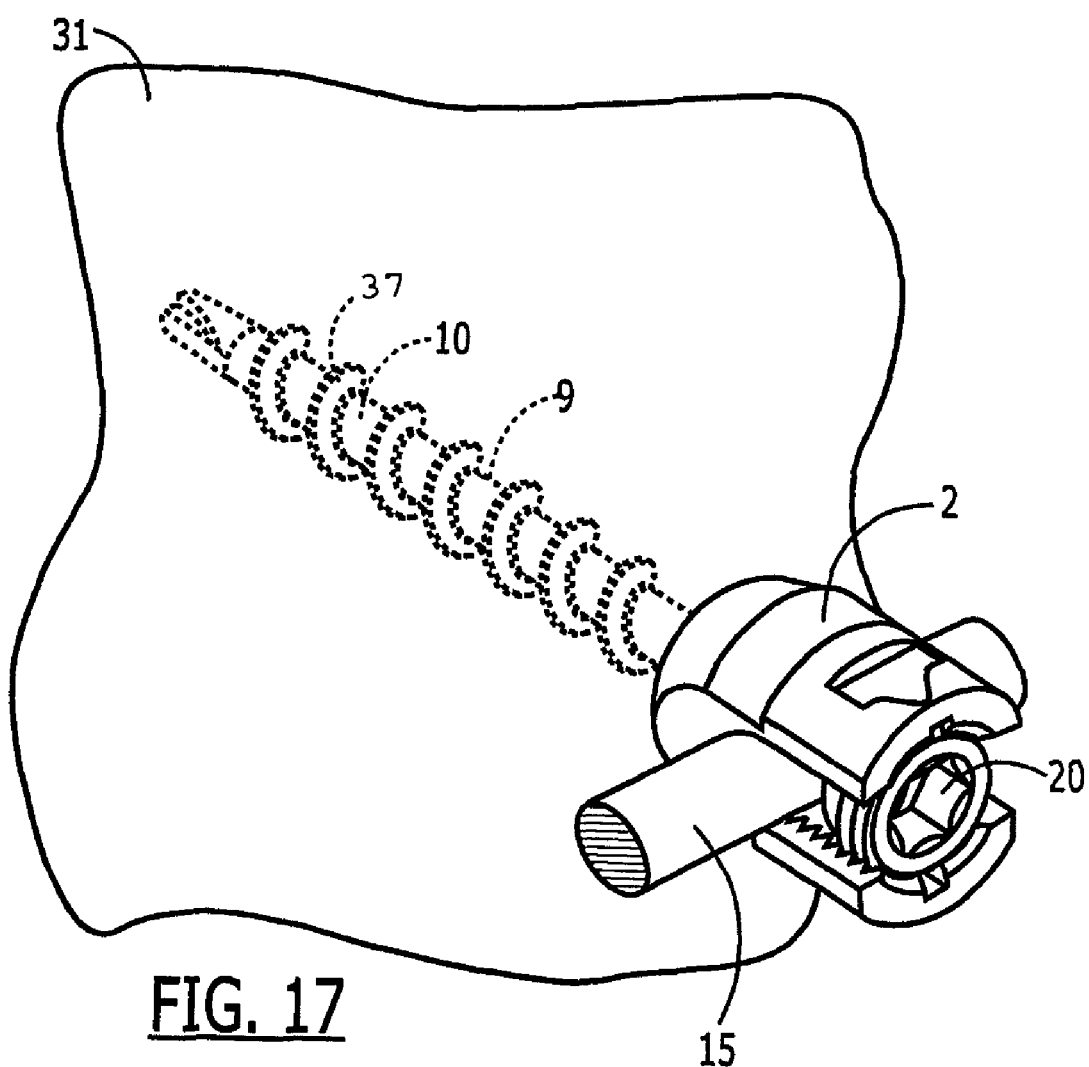
FIG. 17 is a plan view of the spinal fixation system of the present invention installed in a bone in a spine.

Finally, FIG. 17 shows a plan view of the spinal fixation system of the present invention installed in a bone in a spine. To use the spinal fixation system 1 of the present invention, a user positions the bottom end 5 of the coupling element 2 adjacent to a bone 31 of a spine. Then, the user inserts the bone fixation element 9 into the coupling element 2 such that a shank 10 is located within the interior space 32 and the tip 38 extends into the hole 13 and is adjacent to the bone 31. The user then drives the bone fixation element 9 into the bone 31 such that at least a portion of a shank 10 extends through the hole 13 and into the bone 31. The bone fixation element 9 may be driven into the bone 31 via various methods, such as, but not limited to, rotation or impact of the bone fixation element 9.

The fixation rod 15 is then admitted into the apertures 17. The wings 27 of the securing element 18 is then inserted into the slots 8 and, finally, the securing element 18 is secured within the coupling element 2 to prevent rotation of the securing element 18 about the longitudinal axis 7 thereof. Additionally, when the securing element 18 is secured within the coupling element 2, a predetermined amount of force is applied on the fixation rod 15 to reduce both rotational and lateral movement thereof within the coupling element 2.

If threads 37 are provided on the bone fixation element 9, then an additional amount of force may be required when driving the bone fixation element 9 into the bone 31. However, use of bone fixation elements 9 having threads 37 thereon provide greater retention of the spinal fixation system 1 within the bone 31.

If the spinal fixation system 1 of the present invention includes both a locking element 20 rotatingly secured to the securing element 18 and a mating element 19 located on the interior surface 3 of the coupling element 2, then, after the user positions the wing 27 on the securing element 18 within at least a portion of the slot 8 of the coupling element 2, the user rotates the locking element 20 such that the mating element 19 of the locking element 20 mates with the mating element 19 of the coupling element 2.

If the spinal fixation system 1 of the present invention includes a retaining element 22, the user inserts the retaining element 22 within the coupling element 2 after insertion of the bone fixation element 9 and prior to insertion of the fixation rod 15 into the coupling element 2 such that the retaining element 22 is located between the bone fixation element 9 and the fixation rod 15. If the retaining element 22 includes wings 26, then the wings 26 are positioned within the slots 8 of the coupling element 2 prior to insertion of the retaining element 22 within the coupling element 9.

If the retaining element 22 is utilized and the diameter 16 of the fixation rod 15 is such that the wings 27 of the securing element 18 either (1) make contact with the wings 26 of the retaining element 22 after the securing element 18 makes contact with the fixation rod 15 or (2) do not make contact with the wings 26 of the retaining element 22 after the securing element 18 makes contact with the fixation rod 15, then a predetermined amount of force is applied on the fixation rod 15, which prevents lateral and rotational movement of the fixation rod 15, and a predetermined amount of force is applied on the retaining element 22 and, in turn, on the head 11 of the bone fixation element 9, thereby resulting in a reduction of movement of the bone fixation element 9.

In the alternative, if the diameter 16 of the fixation rod 15 is such that the wings 27 of the securing element 18 make direct contact with the wings 26 of the retaining element 22 prior to the securing element 18 directly contacting the fixation rod 15, then lateral and rotational movement of the fixation rod 15 is permitted. However, a predetermined amount of force is applied on the retaining element 22 and, in turn, on the head 11 of the bone fixation element 9, thereby resulting in a reduction of movement of the bone fixation element 9.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A spinal fixation system for use in the fixation of a spine comprising:
    a coupling element having:
        a pair of opposed longitudinal apertures through a wall thereof extending from a top end of the coupling element to an aperture bottom in spaced relation from a bottom end of the coupling element, the wall defining an interior space dimensioned for admitting a bone fixation element thereinto, the apertures dimensioned for admitting a fixation rod diametrically through the interior space;
        a longitudinal slot in an interior surface of the coupling element extending from the coupling element top end to a slot bottom in spaced relation from the coupling element bottom end; and
        a hole through the bottom end dimensioned for admitting a shank of the elongated bone fixation element therethrough and smaller than a head of the bone fixation element for retaining the head within the interior space, the shank extending downwardly from the bone fixation element;
    a securing element dimensioned for vertical slidable insertion into the coupling element interior space atop the fixation rod, the securing element having an outwardly extending wing dimensioned for riding in the coupling element slot, for preventing a rotation of the securing element about a longitudinal axis thereof, an upwardly extending arm dimensioned for insertion into a locking element; a locking element comprising a mating element located circumferentially about an external surface thereof, a wall defining a locking element interior space, the space further comprising a groove therein for rotatably receiving and retaining the upwardly extending arm of the securing element, the mating element configured to mate with a complimentary mating element located on an interior surface of the coupling element; and a retaining element dimensioned for insertion into the coupling element interior space atop the bone fixation element head, the retaining element for retaining the fixation rod within the interior space, wherein the retaining element has an outwardly extending wing dimensioned for riding in the coupling element slot, for preventing a rotation of the retaining element about a longitudinal axis thereof.

2. The spinal fixation system of claim 1 wherein:
    the retaining element has a substantially concave top surface dimensioned for at least partially circumscribing the fixation rod.

3. The spinal fixation system of claim 1 wherein:
    the retaining element has a substantially concave top surface dimensioned for at least partially circumscribing the fixation rod.

4. The spinal fixation system of claim 1 wherein:
    the securing element has a substantially concave bottom surface dimensioned for at least partially circumscribing the fixation rod.

5. The spinal fixation system of claim 1 wherein:
    the securing element has a substantially concave bottom surface dimensioned for at least partially circumscribing the fixation rod.

6. The spinal fixation system of claim 1 wherein:
    the hole is dimensioned for housing a substantially round bone fixation element head, for permitting rotational movement of the bone fixation element.

7. The spinal fixation system of claim 1 wherein:
    the retaining element has a bottom surface dimensioned for housing a substantially round bone fixation element head, for permitting rotational movement of the bone fixation element.

8. A spinal fixation system for use in the fixation of a spine comprising:
    a coupling element having:
        a pair of opposed longitudinal apertures through a wall thereof extending from a top end of the coupling element to an aperture bottom in spaced relation from a bottom end of the coupling element, the wall defining an interior space dimensioned for admitting a bone fixation element thereinto, the apertures dimensioned for admitting a fixation rod diametrically through the interior space;
        a longitudinal slot in an interior surface of the coupling element extending from the coupling element top end to a slot bottom in spaced relation from the coupling element bottom end; and
        a hole through the bottom end dimensioned for admitting a shank of the elongated bone fixation element therethrough and smaller than a head of the bone fixation element for retaining the head within the interior space, the shank extending downwardly from the bone fixation element;
    a mating element located on an interior surface of the coupling element adapted for mating with a locking element, the locking element for retaining the fixation rod within the interior space and comprising a wall defining a locking element interior space, the wall further comprising a grove therein;
    a securing element dimensioned for vertical slidable insertion into the coupling element interior space atop the fixation rod, the securing element having an outwardly extending wing dimensioned for riding in the coupling element slot, for preventing a rotation of the securing element about a longitudinal axis thereof, and an upwardly extending arm dimensioned for rotatable insertion into the groove of the locking element interior space; and
    a retaining element dimensioned for insertion into the coupling element interior space atop the bone fixation element head, the retaining element for retaining the fixation rod within the interior space, having:
        an outwardly extending wing dimensioned for riding in the coupling element slot, for preventing a rotation of the retaining element about a longitudinal axis thereof;
        a substantially concave top surface dimensioned for at least partially circumscribing the fixation rod; and
        a bottom surface dimensioned for housing the substantially round bone fixation element head, for permitting rotational movement of the bone fixation element.

9. The spinal fixation system of claim 8 wherein:
    the hole is dimensioned for housing a substantially round bone fixation element head, for permitting rotational movement of the bone fixation element.

10. A method for fixating a spine comprising:
    positioning a bottom end of coupling element having a pair of opposed longitudinal apertures through a wall thereof extending from a top end of the coupling element to an aperture bottom in spaced relation from the bottom end of the coupling element, the wall defining an interior space dimensioned for admitting a bone fixation element thereinto, the apertures dimensioned for admitting a fixation rod diametrically through the interior space; a longitudinal slot in an interior surface of the coupling element extending from the coupling element top end to a slot bottom in spaced relation from the coupling element bottom end; and a hole through the bottom end dimensioned for admitting a shank of the elongated bone fixation element therethrough and smaller than a head of the bone fixation element for retaining the head within the interior space, the shank extending downwardly from the bone fixation element adjacent to a bone in a spine;

inserting a bone fixation element into the coupling element such that a shank of the bone fixation element is located within the interior space and the tip extends into the hole and is adjacent to the bone;

driving the bone fixation element into the bone such that at least a portion of a shank of the bone fixation element extends through the hole and into the bone; inserting an outwardly extending wing of a retaining element into the coupling slot and atop the bone fixation element head, the retaining element for retaining the bone fixation rod within the interior space admitting a fixation rod into a pair of opposed longitudinal apertures though a wall of the coupling element;

inserting an outwardly extending wing of a securing element into the coupling element slot, wherein the outwardly extending wing is dimensioned for riding in the coupling element slot; and securing the securing element within the coupling element to prevent rotation of the securing element about a longitudinal axis thereof and mating a locking element comprising a wall defining an internal locking space and grove therein with an upwardly extending arm of the securing element such that the upwardly extending arm is secured within the groove; and mating the locking element with a mating element located on an interior surface of the coupling element, for retaining the fixation rod within the interior space.

\* \* \* \* \*